US00PP21541P3

(12) United States Plant Patent
Cook

(10) Patent No.: US PP21,541 P3
(45) Date of Patent: Nov. 30, 2010

(54) ***GARDENIA* PLANT NAMED 'STAR DUST'**

(50) Latin Name: ***Gardenia jasminoides Ellis×G. thunbergia* L.**
Varietal Denomination: Star Dust

(75) Inventor: Allyn Cook, 109 SW. 101 Ct., Gainesville, FL (US) 32607

(73) Assignee: Allyn Cook, Gainesville, FL (US)

( * ) Notice: Subject to any disclaimer, the term of this patent is extended or adjusted under 35 U.S.C. 154(b) by 438 days.

(21) Appl. No.: 11/891,789

(22) Filed: Aug. 13, 2007

(65) Prior Publication Data

US 2009/0049575 P1 Feb. 19, 2009

(51) Int. Cl.
*A01H 5/00* (2006.01)

(52) U.S. Cl. ..... Plt./255

(58) Field of Classification Search ..... Plt./255, Plt./225

See application file for complete search history.

(56) References Cited

U.S. PATENT DOCUMENTS

PP15,189 P3 * 9/2004 Barendse ..... Plt./255

OTHER PUBLICATIONS

MPEP Chapter 1600.*

E-mail communication from Sep. 18, 2009.*

* cited by examiner

*Primary Examiner*—Wendy C. Haas

(57) ABSTRACT

A new and distinct *gardenia* named 'Star Dust' that is resistant to race 2 of the root knot nematode and has dark green, glossy leaves and fragrant white flowers typical of the genus is described.

8 Drawing Sheets

Figure 1:
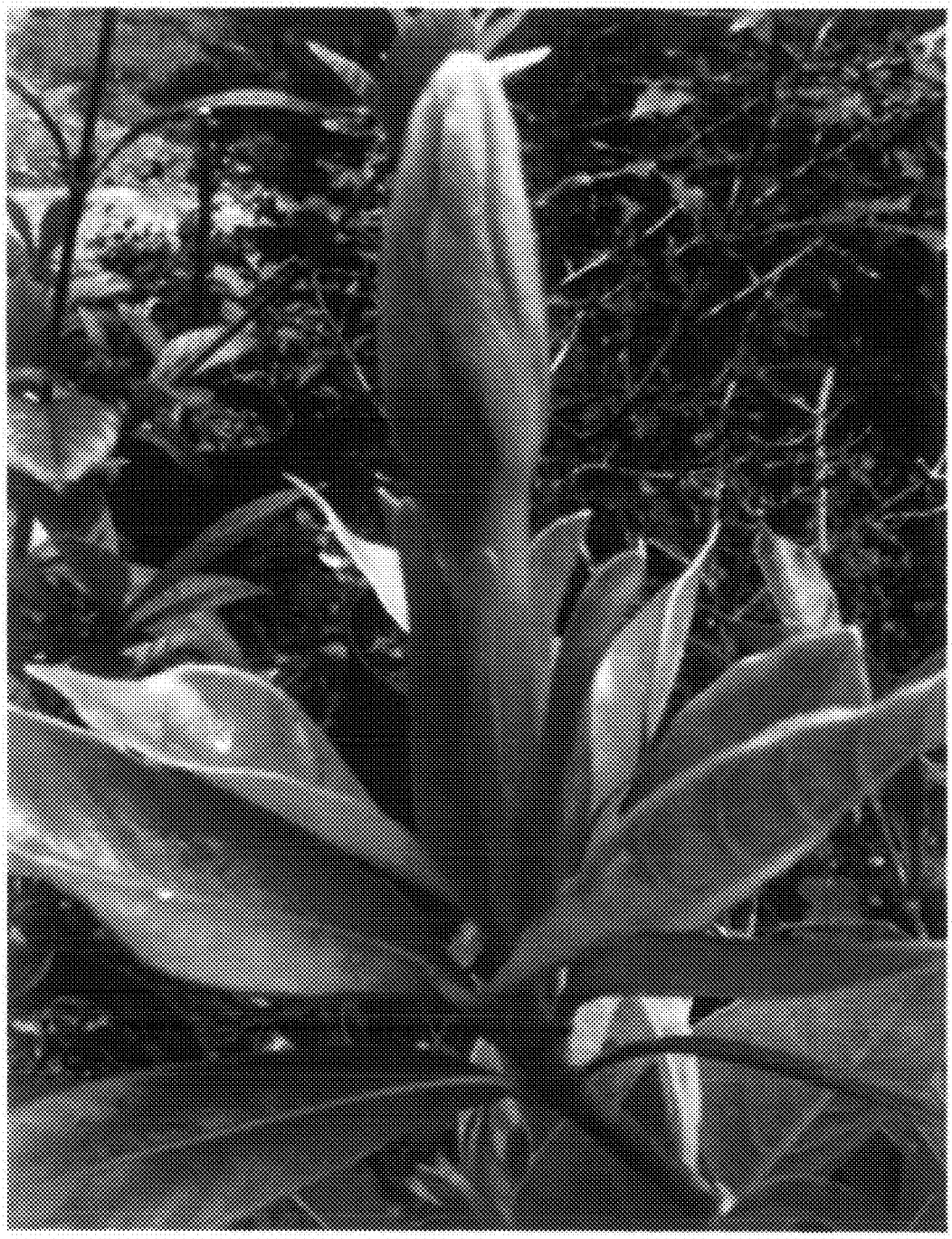

Botanical designation: *Gardenia jasminoides Ellis×G. thunbergia* L.

Varietal denomination: 'Star Dust'.

BACKGROUND OF THE INVENTION

*Gardenia* (*Gardenia jasminoides*) has been a favorite landscape plant in the warmer areas of the United States for more than a century. Popularity of the species has been encouraged, in large part, by the attractiveness of the plants and the allure of the pleasantly aromatic flowers. Additionally, the species is quite adaptable to various cultural methods and has modest to long-term life expectancy. There is a consistent lack of seed production in most cultivars despite frequent production of pollen and pistillate structures which leads to the presumption that most present-day cultivars have originated as asexual deviants. The species has few important cultural problems other than nematode infestation for which no cultivars of *G. jasminoides* are known to exhibit tolerance. Thus, a sizeable share of the plants produced for retail sale are now grafted onto stocks of *G. thunbergia,* the only recognized nematode-resistant species of the genus, and the price to consumer must reflect this additional production cost. Unfortunately, this rootstock species is intolerant of freezing temperatures which thereby limits outdoor culture of grafted plants to zone 8 or warmer.

All plants for the project herein described were grown in the open at the address given above. Ambient air temperature during the duration of this period ranged from approximately 4-22 C in winter to 22-34 C in summer with occasional, sometimes consecutive, nights of −5 C from January-March. Supplemental irrigation as needed was obtained from the local water service. Early in this study the water tested approximately ph 7+ but was later changed to about ph 6.5. Test plants for nematode screening were grown in new plastic pots in a modification of the local 'Traxler Mix' that included only soil and sand with no more than 5% (by volume) 'pearlite' and no pine bark or peat. All pots were placed on new, black plastic ground cover and given quarterly 8-8-8 fertilizer with minor elements by hand.

The discovery of a reliable seed-producing cultivar of *G. jasminoides,* i.e. 'Star Bright' made possible horticultural improvement through controlled breeding. In 2003, a pollination on 'Star Bright' was made with pollen from *G. thunbergia* and the resulting seedlings all were first exposed to Southern root-knot nematode (*Meloidogyne incognita*, race 2) in 2004. Inoculum for each of these inoculations was prepared by laboratory staff of the Nematology Department, University of Florida, Gainesville, Fla. Three years later the plant herein described was found to have the basic horticultural features of desirable cultivars as well as demonstrated resistance to nematode infestation.

SUMMARY OF THE INVENTION

The 'Star Dust' plant exhibits various physical attributes that resemble, in part, both parental types. Mature, blooming plants may reach one meter in height and width with moderately open habit more resembling the pistillate parent than the pollen parent.

BRIEF DESCRIPTIONS OF DRAWINGS

FIG. 1 Side-view of 'Star Dust' flower bud and extended corolla tube.

Figure 2:
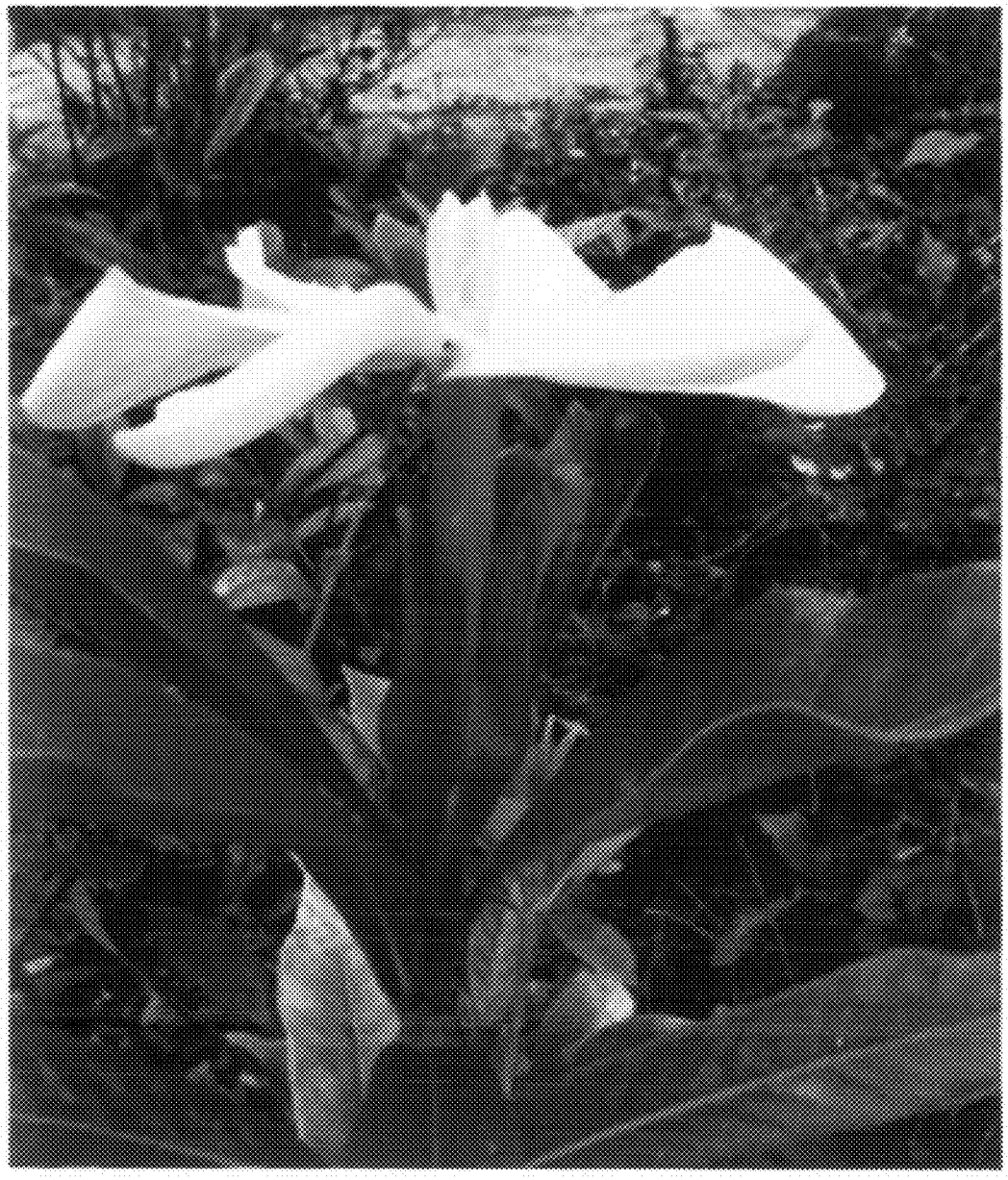

FIG. 2 Mature flower of 'Star Dust' plant shows a single whorl of petals.

Figure 3:
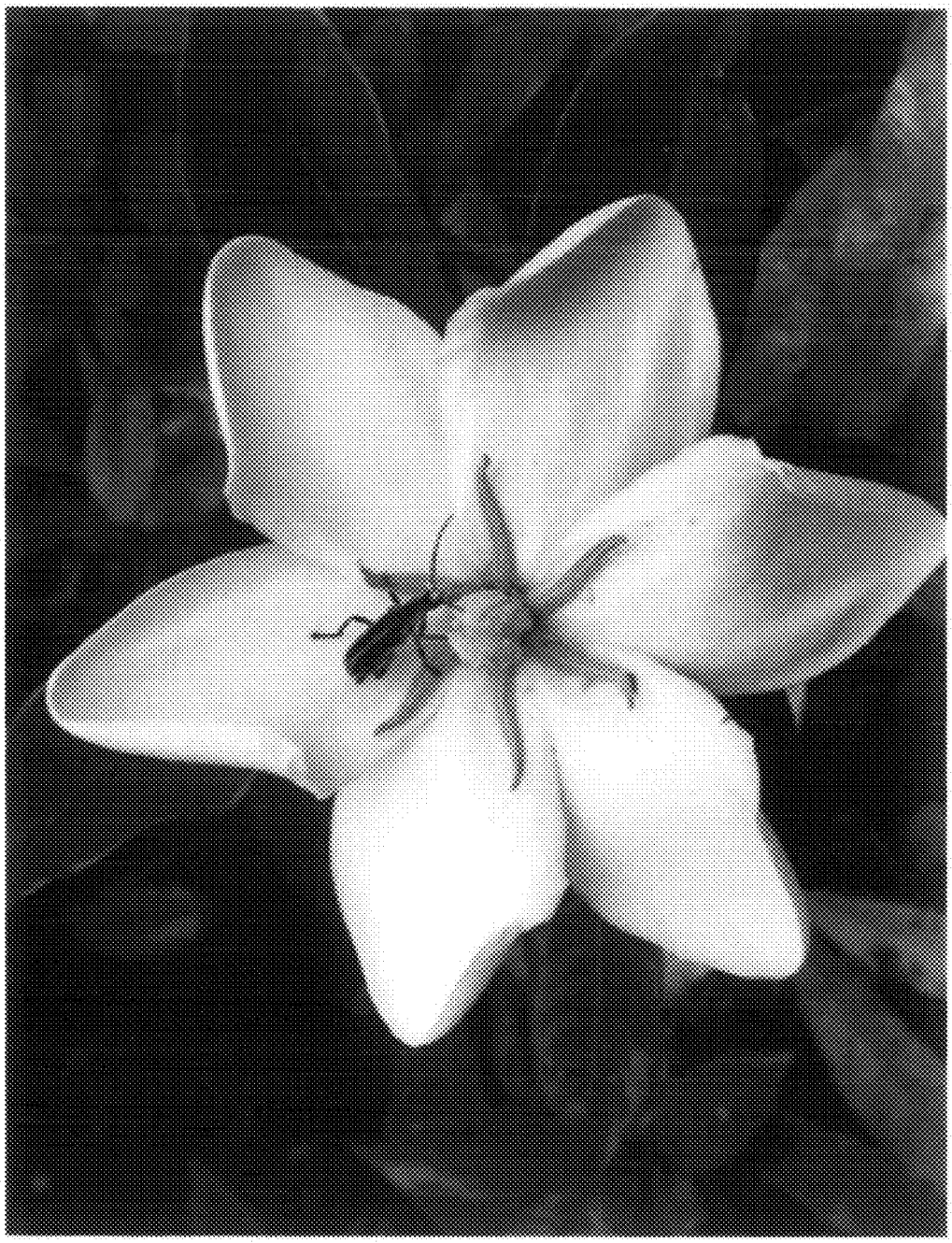

FIG. 3 Top view of 'Star Dust' flower petals after anthesis.

Figure 4:
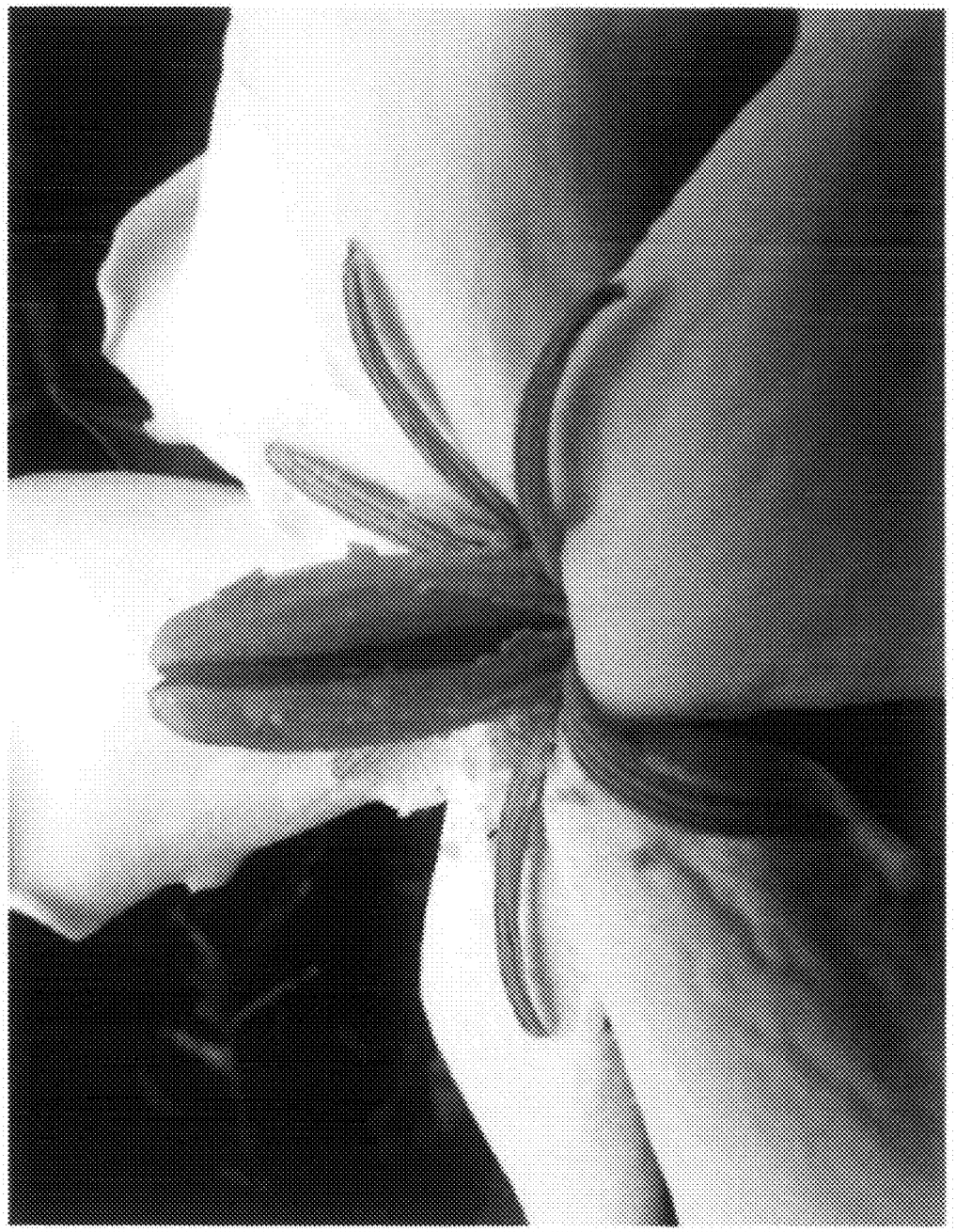

FIG. 4 Side view of pistillate structure of 'Star Dust' flower showing exposed suture.

Figure 5:
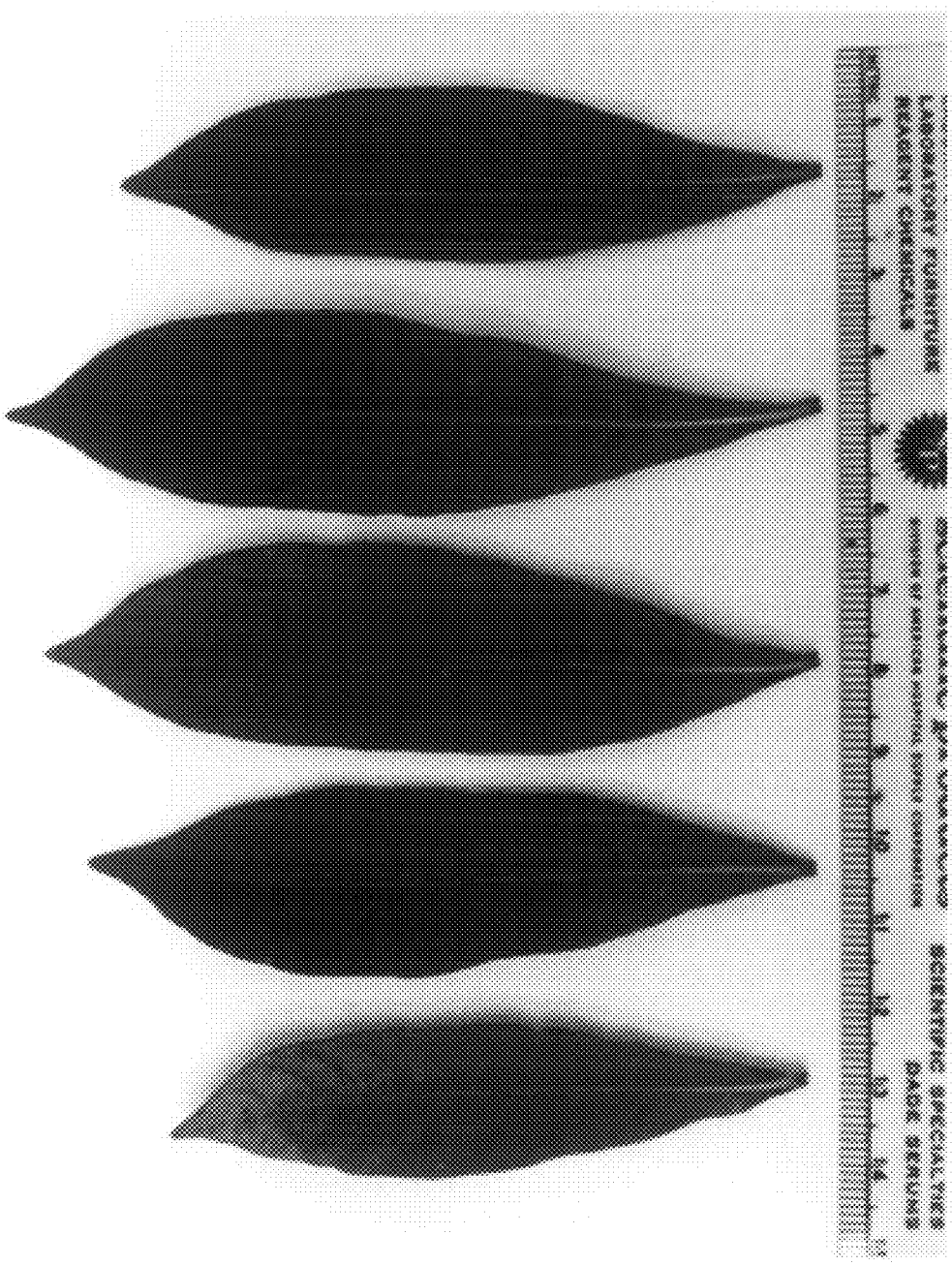

FIG. 5 Upper side view of 'Star Dust' leaves.

Figure 6:
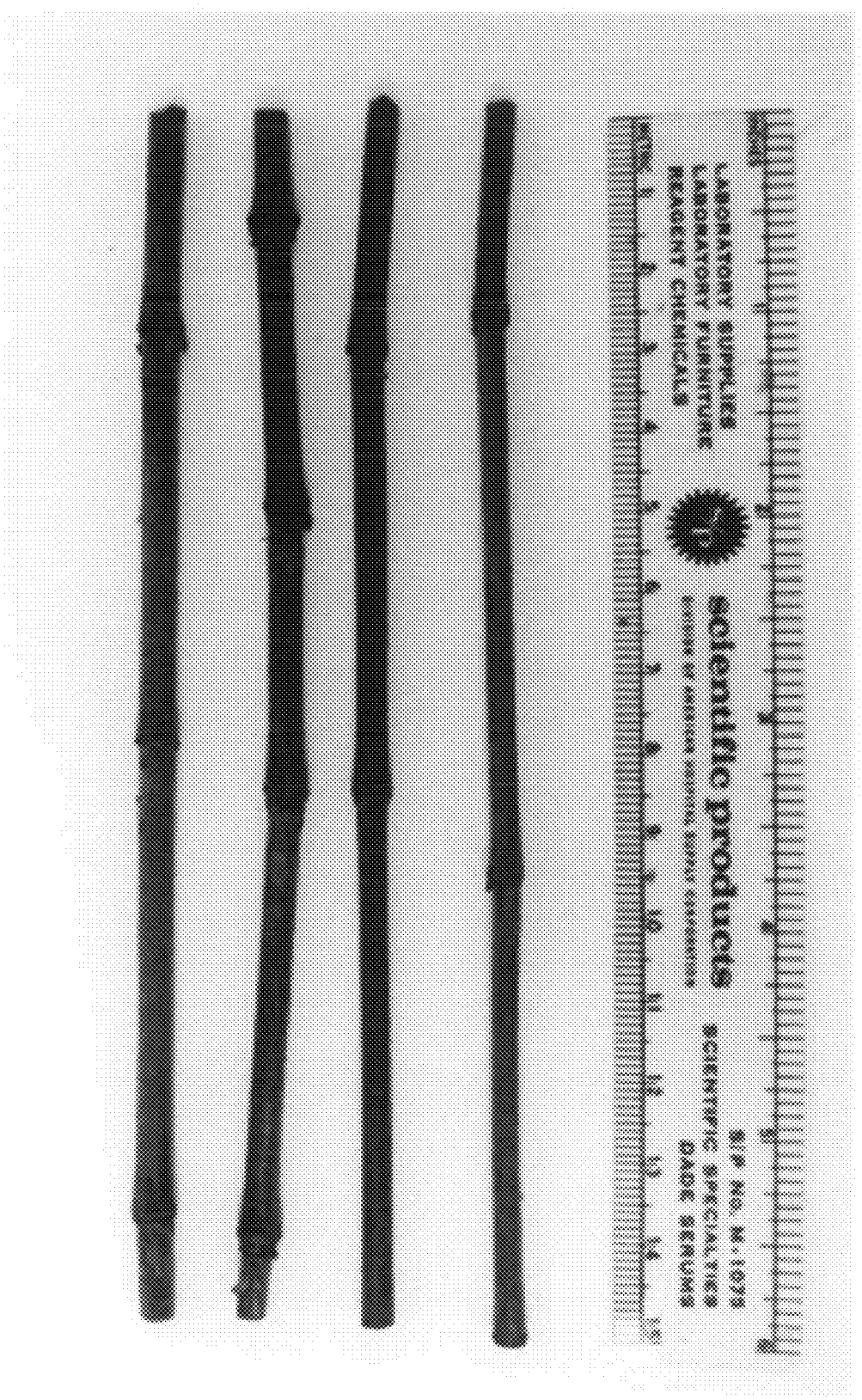

FIG. 6 Bark/bud features of young stems of 'Star Dust' plant.

Figure 7:
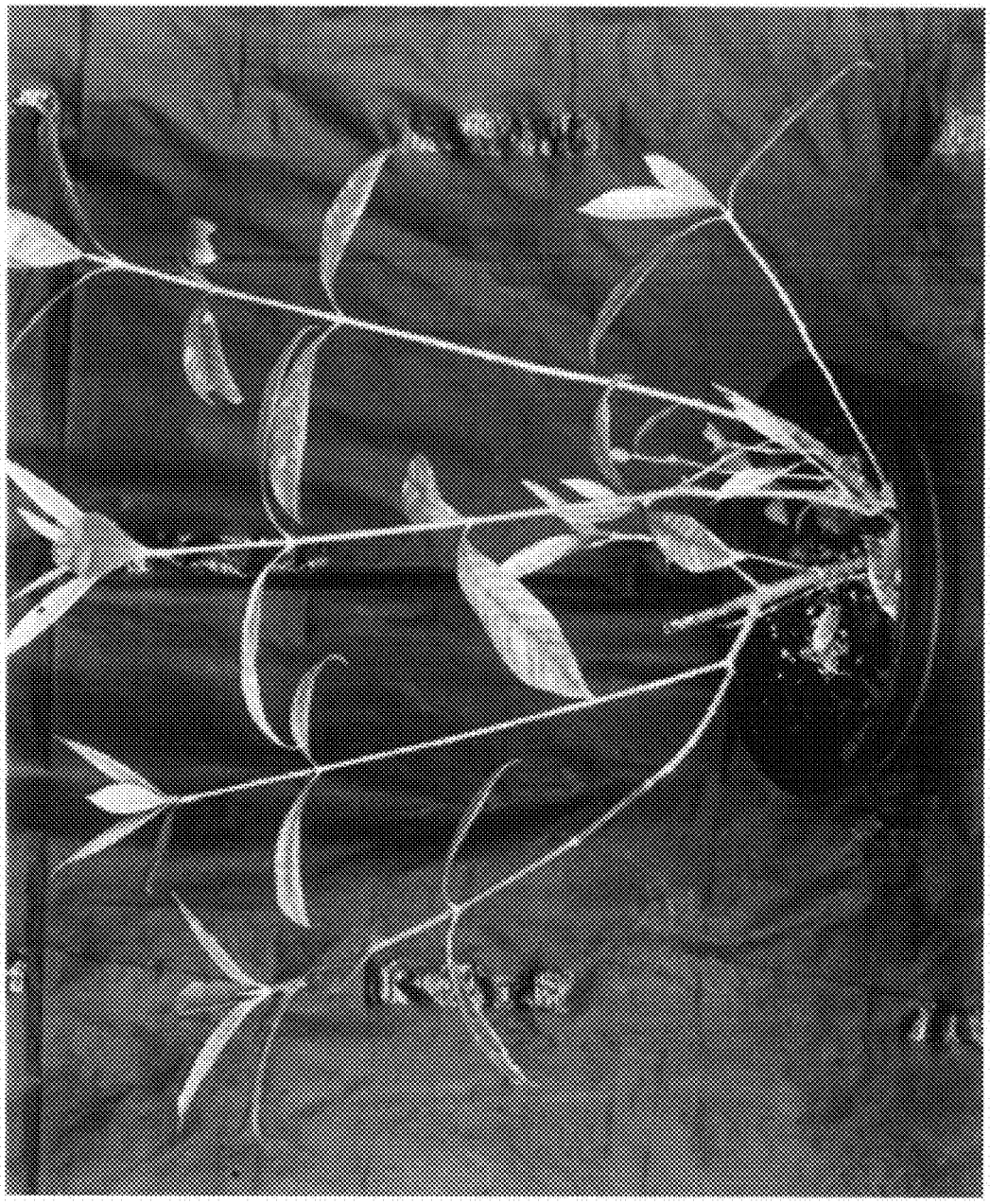

FIG. 7 Whole plant view of 'Star Dust' plant under test.

Figure 8:
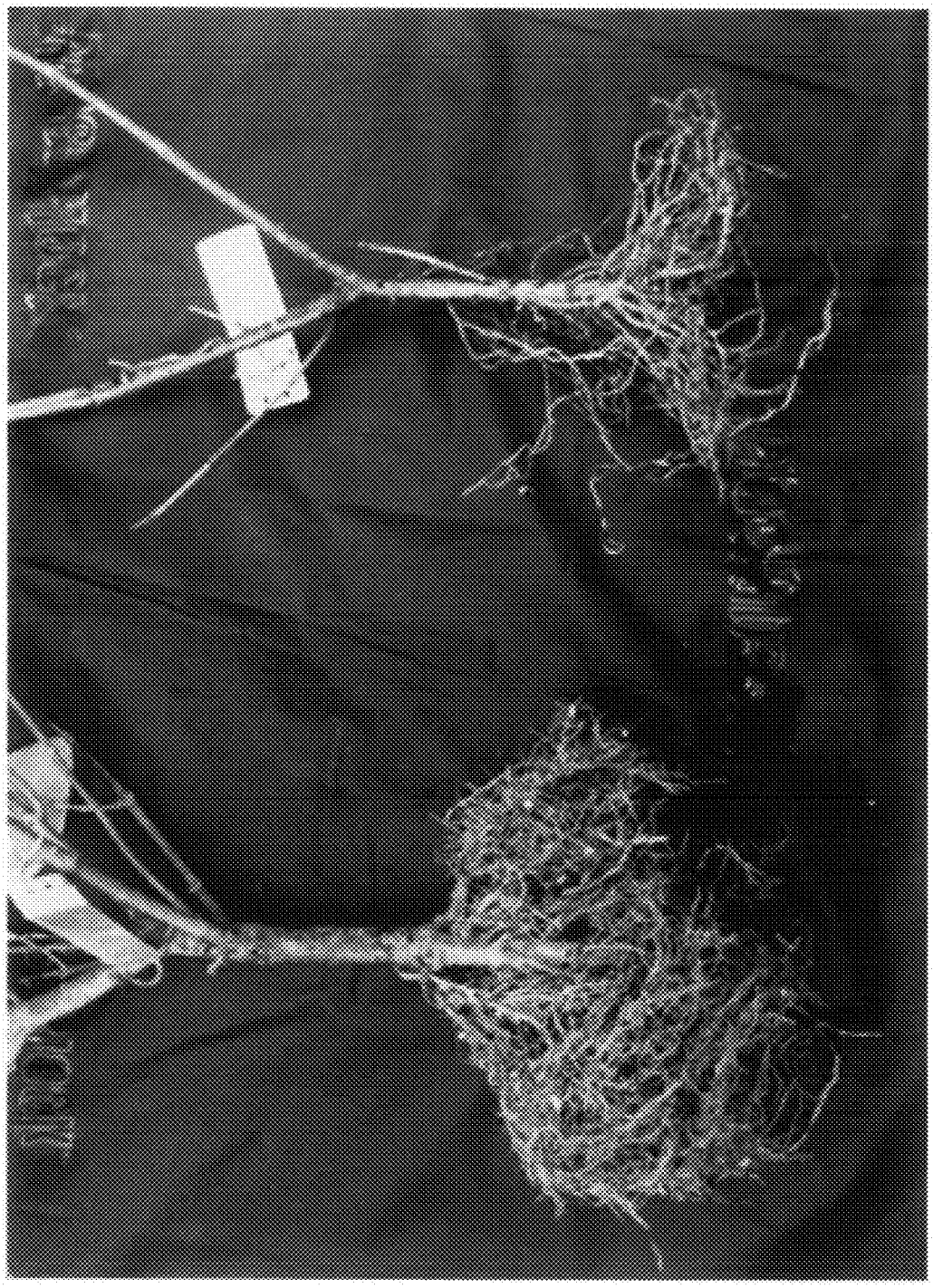

FIG. 8 Root systems of 'Star Dust' (left) and 'susceptible check' (right) plants under test to determine responses to nematode infestation.

DETAILED BOTANICAL DESCRIPTION

Branches are essentially straight with usually at least 10 cm between nodes and young bark light green that darkens to medium brown with age (FIG. 6). Such branching gives the plant an upright appearance quite unlike the pollen parent that has much stouter branching that shows no particular organization and gives each plant an irregular growth habit with some of the secondary branches growing at 90 degrees from the supporting branch. The young bark on the pollen parent plant is simply lighter gray than bark on older limbs and the entire plant gives an unorganized appearance. All branching parts of the pollen parent plant are essentially inflexible. Diameter of even small branches on the pollen parent is considerably greater than those of the pistillate parent and main stems may reach 2.5-4.0 cm.

Leaves on the 'Star Dust' plant are nearly identical to those of the pistillate parent (FIG. 5). Mature leaf size may reach 5.5×15.0 cm with a width:length ratio of 0.35 and venation more clearly visible from below with only moderate mesophyll puckering in the interstitial areas from above. Leaf shape is consistently ovate but both margins are slightly recurved at the distal end to form an acuminate tip. Young leaves are light green in color and characteristically have a glossy sheen that is not so obvious on the young stems. The sheen on leaves may remain on well fertilized plants while the stems gradually turn to brown as they age. Leaves on the pollen parent are flat, thin and fragile with venation obvious from both upper and lower sides but more raised underneath and typically cordate to bellows shaped with a 0.5 width: length ratio.

Foliar symptoms of nematode infestation in *gardenia* are slow to develop and less than distinctive until the root system is severely damaged. The 'Star Dust' plant in FIG. 7 was left unfertilized for more than a year so as not to discourage nematode infection. The cumulative root damage in 'Star Dust' compared to a susceptible plant is illustrated in FIG. 8.

Flowering in the 'Star Dust' plant illustrates the contribution of characters from both parental types. Timing of flower production in the hybrid is between that of the parental types, i.e. 2-4 weeks later than 'Star Bright' and 2-4 weeks earlier than *G. thunbergia*. Flowers are sessile on young branches or terminal ends of branches and have a light green colored corolla tube of 1×5 cm set in a dark green calyx cup with 5-6 sepal-like structures appressed upward against the base of the corolla tube (FIG. 1). The flower bud may enlarge to 1.5×3 cm before opening as petals expand into a single whorl that may reach 5-7 cm in diameter (FIG. 2.) At anthesis, the anthers, originally closely appressed to the pistillate structure and placed alternately with the petals, lie flat against the petals after they open but remain attached thereto only in the throat of the corolla tube (FIG. 3). There is abundant pollen released as the anthers recurve from the pistillate structure that extends 6-8 mm above the plane of the expanded petals and exhibits a single, prominent suture approximately 2 mm wide that is continuous from one side to the other of the pistillate structure (FIG. 4.). Except for the lengthy corolla tube, absent in the flower of the pistillate parent, flower structure and formation is identical to that of the pistillate parent.

Young, brown wood cuttings of 'Star Dust' root readily in the soil mixture described above under mild, outdoor conditions, i.e. spring months, in Gainesville as has been demonstrated repeatedly.

'Star Dust' has been proven both self- and cross-fertile but the pattern of heritability for desirable characters, including flower production, remains to be determined. Retention of the described traits of 'Star Dust' can be assured only by asexual reproduction.

Coloration:

The colors cited are set forth with reference to The Royal Horticultural Society Colour Chart, 1996 edition.

The upper surface of the leaves appears to be about RHS 147A.

The bloom coloration appears to be about RHS 155C.

I claim:

1. A new and distinct variety of *Gardenia* plant, as herein illustrated and described.

* * * * *